US00PP34910P2

(12) United States Plant Patent
Hansen

(10) Patent No.: US PP34,910 P2
(45) Date of Patent: Jan. 10, 2023

(54) ***AGASTACHE* PLANT NAMED 'ROYAL RASPBERRY'**

(50) Latin Name: ***Agastache* hybrid**
Varietal Denomination: Royal Raspberry

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,305

(22) Filed: Apr. 28, 2022

(51) Int. Cl.
*A01H 5/02* (2018.01)
*A01H 6/50* (2018.01)

(52) U.S. Cl.
USPC ..... Plt./399
CPC ..... *A01H 6/50* (2018.05)

(58) Field of Classification Search
USPC ..... Plt./384
CPC ..... A01H 5/02
See application file for complete search history.

*Primary Examiner* — Kent L Bell

(57) ABSTRACT

A new and unique cultivar of hyssop, *Agastache* plant named 'Royal Raspberry' with medium-sized, dense, mounded, well-branched habit and spring foliage color with burgundy cast. The large flowers of rosy-purple coloration begin in early summer and cover the top two-thirds of the plant. The effective flowering season is extended with burgundy-colored calyxes in densely branched panicles. The new plant is useful in the landscape and as a cut flower.

1 Drawing Sheet

Botanical denomination: *Agastache* hybrid.
Variety designation: 'Royal Raspberry'.

STATEMENT REGARDING PRIOR DISCLOSURES UNDER 37 CFR 1.77(b)(6)

The first non-enabling disclosure of the claimed plant was made by Walters Gardens, Inc. on Dec. 1, 2021, in the form of a website brief description and photograph followed by a short description. The first enabling disclosure of a sale of the claimed plant was on May 17, 2021, by Walters Gardens, Inc to Casertano Greenhouses and Farms, Inc. Walters Gardens, Inc. obtained the new plant and information about the new plant directly from the inventor. No plants of *Agastache* 'Royal Raspberry' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct hyssop plant or anise hyssop from the genus *Agastache* and given the cultivar name 'Royal Raspberry'. The new plant was the result of a single seedling selection from a self-pollination on Jul. 15, 2015, by the inventor of the proprietary, unreleased, hybrid, clone *Agastache* 14-8-1 (not patented). The seeds from the self-pollination were collected in late summer of 2015. The individually selected seedling was eventually given the breeder code 15-12-38 after being first isolated from trials at a nursery in Zeeland, Mich. during the summer of 2017. It was selected for the final introduction in the summer of 2019.

*Agastache* 'Royal Raspberry' has been asexually propagated at the same nursery in Zeeland, Mich. using traditional shoot tip and stem cutting procedures and found to reproduce plants that are identical and exhibit all the characteristics of the original plant in successive generations of asexual propagation.

The new plant, *Agastache* 'Royal Raspberry', has not been observed under all possible environments. The phenotype may vary slightly with different environmental conditions, such as temperature, light, fertility, moisture and maturity levels, but without any change in the genotype.

In comparison to the new plant, the parent is shorter and more mounded in habit and the flower color is a lighter lavender-pink.

The nearest comparison varieties known to the inventor are: 'Mango Tango' U.S. Plant Pat. No. 25,747, 'Rosie Posie' U.S. Plant Pat. No. 25,857, 'Kudos Ambrosia' U.S. Plant Pat. No. 25,616, 'Kudos Mandarin' U.S. Plant Pat. No. 25,381, 'Summer Sunset' U.S. Plant Pat. No. 23,623, 'Ava' (not patented), 'Desert Solstice' (not patented), 'Desert Sunrise' (not patented) and 'Bolero' (not patented).

'Mango Tango' has a significantly smaller habit in both height and width and has flowers that are light-peach to dusky-orange. 'Rosie Posie' has a shorter and more compact habit, and the flowers are hot-pink colored. 'Kudos Ambrosia' has lighter-pink flowers from orangish-peach buds and the calyxes are not as dark. 'Kudos Mandarin' has deeper-orange-colored flowers with a significantly smaller habit 'Ava' has a height of 120 to 150 cm with a narrow upright habit and flowers that are deep rose-pink. 'Summer Sunset' is less winter-hardy, smaller and narrower in habit, and the flower color contains more orangish coloration. 'Desert Solstice' has a similar height, but more upright narrow habit and flowers that are rosy-pink and calyxes that are a rosy fuchsia. 'Desert Sunrise' has a habit that is about 120 cm tall while upright and 60 cm wide with flowers that are a lighter orangish-pink. 'Bolero' has is more mounded in habit and more compact, hut has similar spring foliage color.

The new plant *Agastache* 'Royal Raspberry' is distinct from the parent and all other anise hyssop known to the inventor in the following combined traits:

1. Medium sized, dense, mounded, well-branched habit;
2. Large flowers of rosy-purple coloration in densely branched panicles;
3. Long bloom time with effectiveness extended by persistent, burgundy-colored calyxes;
4. Flowers covering the upper two-thirds of the plant for about five weeks beginning in early summer;
5. Foliage displays a burgundy cast in the spring.

BRIEF DESCRIPTION OF THE DRAWINGS

The photographs of the new plant demonstrate the overall appearance of the plant, including its unique traits. The colors are as accurate as reasonably possible with color reproductions. Ambient light spectrum, temperature, source and direction may cause the appearance of minor variation in color.

DETAILED PLANT DESCRIPTION

Figure 1:
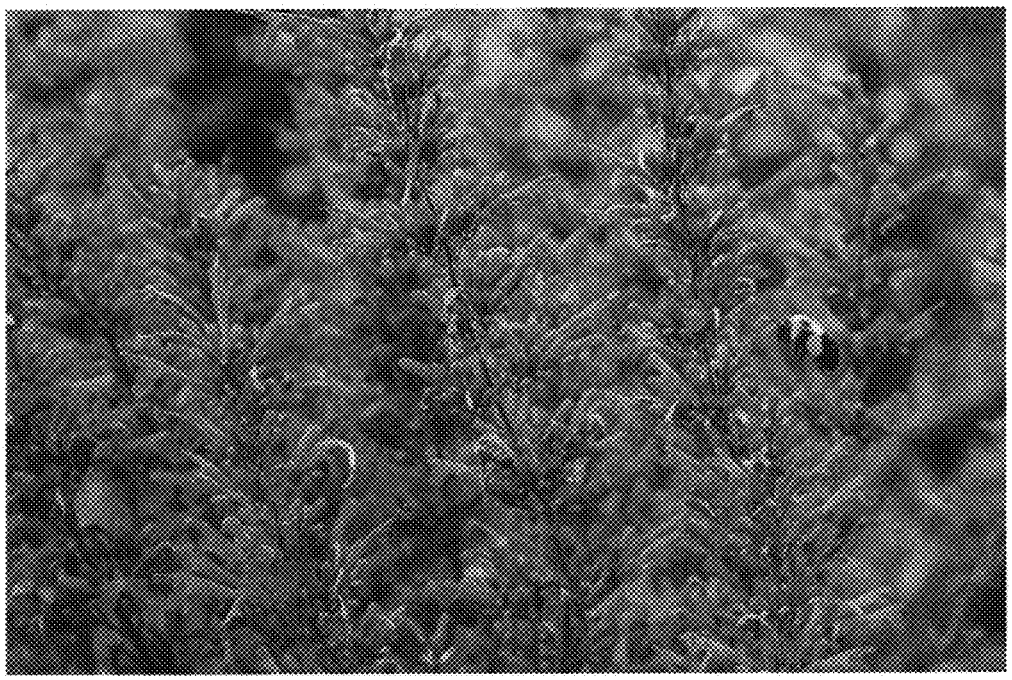
FIG. 1 shows a close-up of the scapes with flowers, buds and calyxes.
Figure 2:
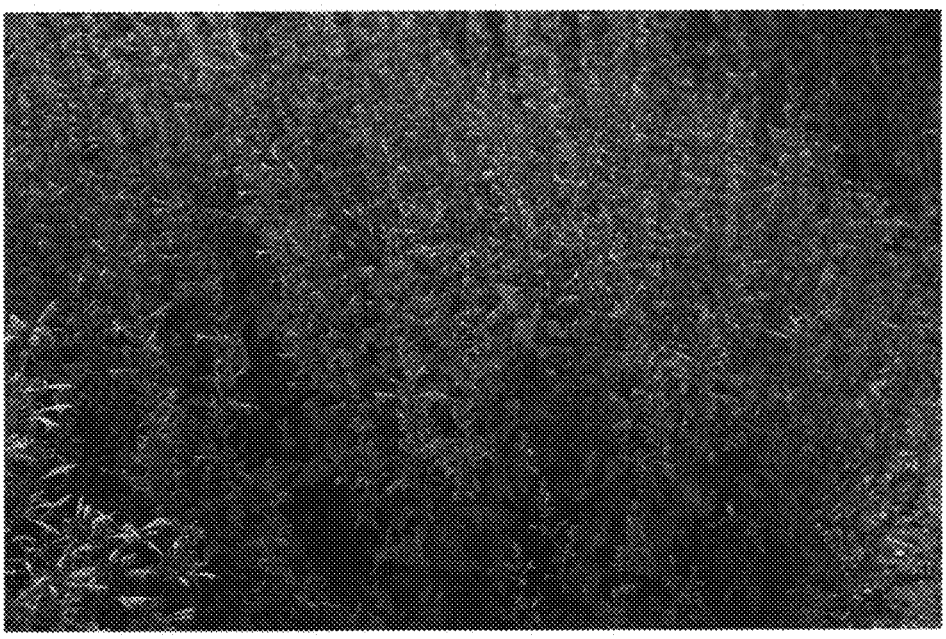
FIG. 2 shows a side view of two-year-old plants in mid-season flower in a trial block at a nursery in Zeeland, Mich.

The following is a detailed description of the new *Agastache* cultivar 'Royal Raspberry' based on observations of two-year-old specimens grown in a display garden at a wholesale perennial nursery in Zeeland, Mich. Color descriptions are from the 2015 edition of The Royal Horticultural Society Colour Chart except where common dictionary terms are used.

Plant habit: Multi-stemmed herbaceous perennial, rounded, heavily branched;

Plant size: Without growth retardants or pinching—to about 81 cm tall and 78 cm across;

Roots: Fibrous, well-branched; to about 2 mm diameter near base; color light tan nearest RHS 165D depending on soil type;

Stem: Quadrangular; fistulous; stiff; wiry; finely pubescent; to about 4 mm across at base and 50 cm tall with flowering starting about 35 cm above soil; ten internodes below branched peduncle; internodes average about 3.5 cm long; about eight to ten stems per plant;

Primary branches: Quadrate; opposite; about ten per plant; to about 31 cm long and about 2.5 mm diameter at base;

Secondary branches: Quadrangular; opposite; up to six per primary branch; to about 40 cm long and 2.5 mm diameter at base;

Stem, primary branch, and secondary branch color: Proximal and distal portions nearest RHS 146C with light to moderate blush of nearest RHS N186C in regions exposed to higher light intensities; nodes nearest RHS N187B;

Leaf: Simple; opposite; broadly lanceolate, base truncate to cordate; apex acute and micro puberulent; margin serrate with eight to nine teeth per side; adaxial and abaxial surfaces micro-puberulent glabrous and matte;

Leaf size: To about 44 mm long and 30 mm near base, decreasing distally;

Leaf venation: Reticulate; glabrous and slightly impressed adaxial, puberulent and costate abaxial;

Leaf color: Young expanding adaxial between RHS 137A with a slight blush of nearest RHS N186C, abaxial nearest RHS N186C with a slight undertone of nearest RHS 146A; mature adaxial nearest RHS 137A with a slight blush of nearest RHS N186C, mature abaxial nearest RHS 147B with a slight blush of nearest RHS N186C;

Vein color: Adaxial nearest RHS 146C, abaxial main proximal veins nearest RHS 148C and distal veins nearest RHS 148B;

Leaf fragrance: Moderately herbal, minty;

Petiole: Concavo-convex; micro-puberulent adaxial and abaxial; to 9 mm long and 2 mm across, average 6 mm long and 1.5 mm;

Petiole color: Adaxial nearest RHS 148C with a light blush of nearest RHS N186C; abaxial nearest RHS 146D;

Inflorescence: In densely branched panicle with short branches or whorls in axils; 8 to 84 flowers on two short branchlets per node; up to 12 nodes per main stem, and up to 1,000 flowers per main stem; flowering portion about 24 cm long and about 7.5 cm across; total flowering portion about 32 cm long and about 33 cm across; each stem flowering for about 5 weeks but remain effective for about 6 weeks or more with strongly-pigmented, persistent, burgundy-colored calyxes;

Bloom period: Early July through early fall in Zeeland, Mich.;

Peduncle: Average about 32 cm tall and about 3 mm at base; puberulent; attitude upward;

Peduncle color: Between RHS 146B and RHS 148B with distal portion nearest RHS N186C;

Pedicel: Cylindrical; short; glabrous; matte; attitude mostly upright; to about 2 mm long and 0.5 mm diameter; color nearest RHS N77A;

Flower: Perfect; complete; zygomorphic; sympetalous; bilabiate, with five sympetalous petals forming an upper lip 2-lobed and lower lip 3-lobed; attitude outwardly to slightly upwardly;

Flower size: About 29 mm long to exerted stamens, about 11 mm tall and 7 mm across; corolla to about 25 mm long, 6 mm tall, and 7 mm across, tube about 3 mm diameter at fusion of two lips;

Flower period: Individual flowers open for about 3 days; individual main panicle lasting for about 5 weeks extending to 6 weeks with branching; and entire plant flowering from early summer to fall;

Bud on day prior to opening: Arcuate; clavate; about 22 mm long, 5.5 mm tall and 4.5 mm wide just before the apex and 2 mm wide at base;

Bud color: Petals nearest RHS 72A toward apex, ventral portion nearest RHS 70B, calyx between RHS N77B and RHS 72A;

Petals: Glabrous adaxial, micro-puberulent abaxial; upper and lower petals proximally fused forming tube in the basal 20 mm long and 3 mm diameter toward fusion of the two petals; both petals matte in both adaxial and abaxial;

Upper 2-lobed petal: About 25 mm long and 4.5 mm across toward apex; lobes centrally cleft about 1 mm deep; lobe apices rounded; margin entire;

Lower 3-lobed petal: About 26 mm long, center lobe to 5 mm long and 7 mm wide; two side lobes to 2 mm long and 4 mm wide; arcuate downward in distal 6 mm; center lobe apex rounded with crenate margin; two side lobes of lower petal spread horizontally, with rounded apex and entire margin;

Petal color: Adaxial and abaxial upper and lower labium between RHS 77B and RHS N78C when initially fully open; just before dropping adaxial and abaxial upper and lower labium between RHS N81B and RHS N81C; adaxial corolla tube basal throat portion nearest RHS N155C and throat distally nearest RHS 84C; abaxial corolla tube basal throat portion nearest RHS NN155C and throat distally between RHS 77B and RHS N78C;

Calyx: About 10.5 mm long and diameter about 3 mm;

Sepals: Five; linear; acute apices; entire margin; to about 10 mm long and 1 mm wide at fusion, fused into tube in basal 9 mm; micro-puberulent outside and glabrous inside; matte both surfaces;

Calyx color: Adaxial proximally between RHS 146D and RHS 145A, distally nearest RHS 146D lightly blushed with nearest RHS 187B; abaxial in high light exposure between RHS 59C and RHS 59B with veins nearest RHS 59B, in shaded position nearest RHS 145A;

Gynoecium: Single; to 30 mm long; exerted;

*Style*.—One, about 28 mm long and about 0.3 mm diameter; terete; glabrous; straight; lustrous; color distal 5 to 7 mm between N79C and RHS N79B, proximally nearest RHS NN155D.

*Stigma*.—Bifid and reflex; each segment about 1 mm long and about 0.2 mm diameter; apices tapering to apoint; color nearest RHS N78B.

*Ovary*.—Superior; about 0.5 mm diameter; color nearest RHS 145A.

Androecium: In two sets of two, exerted;

*Filaments*.—Two longer and two shorter; paired and exerted; adnate to the corolla; longer pair to 29 mm long and adnate in the basal 20 mm and free in the proximal 9 mm; shorter pair to 27 mm long and adnate in the basal 19 mm and free in the proximal 8 mm; color both sets nearest RHS N78D.

*Anthers*.—Dorsifixed; versatile; longitudinal; to about 1 mm long and about 0.7 mm across; color nearest RHS 83B.

*Pollen*.—Abundant; color nearest RHS NN155C.

Fragrance: None detected;

Fruit: Two carpels;

Seed: Nutlet, typically one to two per naturally pollinated flower, globose; about 1 mm diameter;

Seed color: Between RHS 200A and RHS 200B;

Resistance: 'Royal Raspberry' is resistant to *Odocoileus hemionus* browsing, and shows no susceptibility to Downy Mildew (*Perononspora*) but has not been tested or shown resistance to other pests and diseases common to *Agastache*.

Hardiness: The new plant has survived USDA hardiness zones 6 to 10 but has not been tested yet beyond these temperatures.

The invention claimed is:

1. A new and distinct cultivar of *Agastache* plant named 'Royal Raspberry' as herein described and illustrated.

* * * * *